(12) United States Patent
Drenser

(10) Patent No.: US 9,504,649 B2
(45) Date of Patent: *Nov. 29, 2016

(54) METHOD AND COMPOSITIONS FOR GENETIC AND RETINAL DISEASE

(71) Applicant: Retinal Solutions LLC, Keene, NH (US)

(72) Inventor: Kimberly Drenser, Novi, MI (US)

(73) Assignee: Retinal Solutions LLC, Keene, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/834,967

(22) Filed: Aug. 25, 2015

(65) Prior Publication Data

US 2015/0352184 A1 Dec. 10, 2015

Related U.S. Application Data

(63) Continuation of application No. 12/381,777, filed on Mar. 17, 2009, now Pat. No. 9,114,078.

(51) Int. Cl.
| | |
|---|---|
| *A61K 9/00* | (2006.01) |
| *A61K 9/08* | (2006.01) |
| *A61K 9/16* | (2006.01) |
| *A61K 9/50* | (2006.01) |
| *A61K 38/17* | (2006.01) |

(52) U.S. Cl.
CPC ............... *A61K 9/08* (2013.01); *A61K 9/0019* (2013.01); *A61K 9/0048* (2013.01); *A61K 9/0051* (2013.01); *A61K 9/1647* (2013.01); *A61K 9/50* (2013.01); *A61K 38/1709* (2013.01)

(58) Field of Classification Search
CPC .... A61K 9/08; A61K 9/0019; A61K 9/0048; A61K 9/0051; A61K 9/1647; A61K 9/50; A61K 38/1709
See application file for complete search history.

(56) References Cited

U.S. PATENT DOCUMENTS

| | | | |
|---|---|---|---|
| 2007/0196872 A1 | 8/2007 | Bex et al. | 435/7.2 |
| 2010/0129375 A1 | 5/2010 | Junge et al. | 424/145.1 |

FOREIGN PATENT DOCUMENTS

| | | |
|---|---|---|
| EP | 1982180 A2 | 10/2008 |
| WO | 2007092487 A2 | 8/2007 |

OTHER PUBLICATIONS

Ohlmann, A. et al.; "Ectopic Norrin induces growth of ocular capillaries and restores normal retinal angiogenesis in Norrie disease mutant mice": J. Neuroscience; 2005, vol. 25, No. 7; pp. 1701-1710.
Xu, Q. et al.; "Vascular development in the retina and inner ear: control by Norrin and Frizzled-4, a high-affinity ligand-receptor pair"; Cell; 2004, vol. 116; pp. 883-895 (abstract only).
Luhmann, U.F.O. et al.; "Role of the narrie disease pseudoglloma gene in sprouting angiogenesis during development of the retinal vasculature"; Invest. Ophthalmol. Vis. Sci.; 2005; vol. 46; pp. 3372-3382.
Perez-Vilar, J. et al.; "Norrie Disease Protein (Norrin) Forms Disulfide-linked Oligomers Associated with the Extracellular Matrix"; J. Biol. Chem.; 1997; 272; pp. 33410-33415.
Smallwood, P.M. et al.; "Mutational Analysis of Norrin-Frizzled 4 Recognition"; J. Biol. Chem.; 1997; 282; pp. 4057-4068.
Lin, S. et al.; "Norrin attenuates protease-mediated death of transformed retinal ganglion cells"; Molecular Vision; 2009; 15; pp. 26-37.

*Primary Examiner* — Ruixiang Li
(74) *Attorney, Agent, or Firm* — Avery N. Goldstein; Blue Filament Law LLC

(57) ABSTRACT

An inventive method for treatment or prevention of vascular diseases of the retina is provided. A Norrin compound is optionally administered to a subject either directly and/or as expressed by a cell. The presence of the compound is either protective of or therapeutic for a pathological condition of the retina. Preferred pathological conditions are those linked to the absence of or mutation of norrin protein and are preferably Norrie disease, FEVR, or macular degeneration.

8 Claims, 5 Drawing Sheets
(4 of 5 Drawing Sheet(s) Filed in Color)

SEQUENCE LISTING

<160> NUMBER OF SEQ ID NOS: 6

<210> SEQ ID NO 1
<211> LENGTH: 133
<212> TYPE: PRT
<213> ORGANISM: Homo sapiens

<400> SEQUENCE: 1

```
Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Glu Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
    130
```

<210> SEQ ID NO 2
<211> LENGTH: 131
<212> TYPE: PRT
<213> ORGANISM: Mus musculus

<400> SEQUENCE: 2

```
Met Arg Asn His Val Leu Ala Ala Ser Ile Ser Met Leu Ser Leu Leu
1               5                   10                  15

Ala Ile Met Gly Asp Thr Asp Ser Lys Thr Asp Ser Ser Phe Leu Met
            20                  25                  30

Asp Ser Gln Arg Cys Met Arg His His Tyr Val Asp Ser Ile Ser His
        35                  40                  45

Pro Leu Tyr Lys Cys Ser Ser Lys Met Val Leu Leu Ala Arg Cys Glu
    50                  55                  60

Gly His Cys Ser Gln Ala Ser Arg Ser Glu Pro Leu Val Ser Phe Ser
65                  70                  75                  80
```

```
Thr Val Leu Lys Gln Pro Phe Arg Ser Ser Cys His Cys Cys Arg Pro
                85                  90                  95

Gln Thr Ser Lys Leu Lys Ala Leu Arg Leu Arg Cys Ser Gly Gly Met
            100                 105                 110

Arg Leu Thr Ala Thr Tyr Arg Tyr Ile Leu Ser Cys His Cys Glu Glu
        115                 120                 125

Cys Ser Ser
    130

<210> SEQ ID NO 3
<211> LENGTH: 131
<212> TYPE: PRT
<213> ORGANISM: Rattus norvegicus

<400> SEQUENCE: 3

Met Arg Asn His Val Leu Ala Ala Ser Ile Ser Met Leu Ser Leu Leu
1               5                   10                  15

Ala Ile Met Gly Asp Thr Asp Ser Lys Thr Asp Ser Ser Phe Leu Met
            20                  25                  30

Asp Ser Gln Arg Cys Met Arg His His Tyr Val Asp Ser Ile Ser His
        35                  40                  45

Pro Leu Tyr Lys Cys Ser Ser Lys Met Val Leu Leu Ala Arg Cys Glu
    50                  55                  60

Gly His Cys Ser Gln Ala Ser Arg Ser Glu Pro Leu Val Ser Phe Ser
65                  70                  75                  80

Thr Val Leu Lys Gln Pro Phe Arg Ser Ser Cys His Cys Cys Arg Pro
                85                  90                  95

Gln Thr Ser Lys Leu Lys Ala Leu Arg Leu Arg Cys Ser Gly Gly Met
            100                 105                 110

Arg Leu Thr Ala Thr Tyr Arg Tyr Ile Leu Ser Cys His Cys Glu Glu
        115                 120                 125

Cys Ser Ser
    130

<210> SEQ ID NO 4
<211> LENGTH: 1935
<212> TYPE: DNA
<213> ORGANISM: Homo sapiens

<400> SEQUENCE: 4
attcccattt gctagtgcgc tgctgcggcc gcacgcctga ttgatatatg actgcaatgg      60
cactttccca tttgacattc tctctctctc tctccctctc tctctctccc tctctctctc     120
cctctctctc tctccctgtg tcgcttaaac aacagtccta acttttgtgt gttgcaaata     180
taaaaggcaa gccatgtgac agagggacag aagaacaaaa gcatttggaa gtaacaggac     240
ctctttctag ctctcagaaa agtctgagaa gaaaggagcc ctgcgttccc ctaagctgtg     300
cagcagatac tgtgatgatg gattgcaagt gcaaagagta agacaaaact ccagcacata     360
aaggacaatg acaaccagaa agcttcagcc cgatcctgcc ctttccttga acgggactgg     420
atcctaggag gtgaagccat ttccaattt ttgtcctctg cctccctctg ctgttcttct     480
agagaagttt ttccttacaa caatgagaaa acatgtacta gctgcatcct tttctatgct     540
ctccctgctg gtgataatgg gagatacaga cagtaaaacg gacagctcat tcataatgga     600
ctcggaccct cgacgctgca tgaggcacca ctatgtggat tctatcagtc acccattgta     660
caagtgtagc tcaaagatgg tgctcctggc caggtgcgag gggcactgca gccaggcgtc     720
```

```
acgctccgag cctttggtgt cgttcagcac tgtcctcaag caacccttcc gttcctcctg      780
tcactgctgc cggccccaga cttccaagct gaaggcactg cggctgcgat gctcaggggg      840
catgcgactc actgccacct accggtacat cctctcctgt cactgcgagg aatgcaattc      900
ctgaggcccg ctgctgtgtg tggcttctgg atgggacaac tgtagaggca gttcgaccag      960
ccagggaaag actggcaaga aaagagttaa ggcaaaaaag gatgcaacaa ttctcccggg     1020
actctgcata ttctagtaat aaagactcta catgcttgtt gacagagaga gatactctgg     1080
gaacttcttt gcagttccca tctcctttct ctggtacaat ttcttttggt tcattttcag     1140
attcaggcat tttcccccctt ggctctcaat gctgtttggg tttccaacaa ttcagcatta     1200
gtgggaaaaa gtgggccctc atacacaagc gtgtcaggct gtcagtgttt ggtgcacgct     1260
ggggaagaat ttactttgga aagtagaaaa gcccagcttt tcctgggaca tcttctgtta     1320
ttgttgatgt ttttttttac cttgtcattt tggtctaagg ttgccattgc tgctaaaggt     1380
taccgatttc aaagtccaga taccaagcat gtggatatgt ttagctacgt ttactcacag     1440
ccagcgaact gacattaaaa taactaacaa acagattctt ttatgtgatg ctggaactct     1500
tgacagctat aattattatt cagaaatgac ttttttgaaag taaaagcagc ataagaatt      1560 tgtcacagga aggctgtctc agataaaatta tggtaaaatt ttgtaaggga gcagacttt     1620 aaagacttgc acaaatacgg atcctgcact gactctggaa aaggcatata tgtactagtg     1680
gcatggagaa tgcaccatac tcatgcatgc aaattagaca accaagtatg aatctatttg     1740
tgggtgtgct atagctttag ccgtgtcacg ggcatcattc tctaatatcc acttgtccat     1800
gtgaaacatg ttgccaaaat ggtggcctgg cttgtcttct gaacgtttgg ttcaaatgtg     1860
ttttggtcct ggaggctcaa attttgagtt attcccacgt tttgaaataa aaagagtata     1920
ttcaaaaaaa aaaaa                                                      1935

<210> SEQ ID NO 5
<211> LENGTH: 1952
<212> TYPE: DNA
<213> ORGANISM: Mus musculus

<400> SEQUENCE: 5
gatgctccat ggaaaagatc cgagcagtgg gcagaggctg tgagtccccg ataacgagag       60 cgcctaaacat ttccgtggta ttcccatttg ctagagcgct gctgcggcca cacgcctgat     120
tgatatatgc ctgcaatggc acttttccat ttgacactct ccctctctct ctccctctct     180
ctccctctct ctctctccct ctctctccct ctctctccct gggtcgctta aacaacagtc     240
ctaacttttg tgtgttgcaa atataaaagg caagccatgt gacagaggga cagaagaaca     300
aaagcatttg gaagtaacag gacctctttc tagctctcag aaaagtctga agagaaagga     360
gccctgcgtt tcccccaagc tgtgcagcac atactgctgt gatcggttgc aagtgaaaga     420
agcaagagaa attcctgcat acaaaggaca atgacaacca gaaagcggca gccctatcct     480
gctctggcct tgaaagggac tggatcctag gaggtggcag catttccaat ctattgtcct     540
ctgtctccct ctgctgtttt tctggaggag tttcccttta caacaatgag aaatcatgta     600
ctagctgcat ccatttctat gctctccctg ctggccataa tgggagatac agacagcaaa     660
acagacagtt catttctgat ggactctcaa cgctgcatga gacaccatta tgtcgattct     720
atcagtcacc cactgtacaa atgtagctca aagatggtgc tcctggccag atgtgagggg     780
cactgcagcc aggcatcacg ctctgagccc ttggtgtcct tcagcactgt cctcaagcaa     840
cctttccgtt cctcctgtca ctgctgccga ccccagactt ccaagctgaa ggctctgcgt     900
```

-continued

```
ctgcgctgct caggggggcat gcgacttact gccacttacc ggtacatcct ctcctgtcac    960
tgtgaggaat gcagctcctg agacttgctg atgattggct ttctgactgg cacaaccaca   1020
ggagcagttc aacctgccag agacggactg caagaaaag agttaaggca gataaagatg    1080
gagcaagtcc cataggattt tgcatattct tgtcctaaag actcaatgtg cttttgacag   1140
aaagtgactc tgggaacttg cttttcattc ccatctcctt tccctggaag aatttctttt   1200
ggttacttta cagattcagg catttcccct gttggctcta attgtggttt gggtgcctga   1260
cagctctgca ttagtgggaa aatgtggggc cctgtgcaat agcatgtcag gctgttccta   1320
tttggtgcat attagggaaa attttaccta actctcctta ggagatcttt gcttgttgtt   1380
tcccctggtc attttggtct aagatttgcc tctaaagttt cctggtttca agatctggac   1440
acccagtcca tggatgttta gtgaggctta ctcacagcca gctaactgct actaaaataa   1500
ctaacacatg ggttctttta tgtgacagcg ggactcctga ccactatagt aattattcag   1560
aagtgactga ggggatataa atgtggcaga ggaatttata atctgaagcc ttttgtgagg   1620
aagcaggctt tcacacatac acactcaggt ggatcctgca ctgactctgg agaaggcata   1680
cattatactt ggtgtggaga acacaccata ctcataattg agcattagtc aagcatgtag   1740
gaatctactt gtgggtgtgc aatagcttca gccatatctt agctatatcc acctgtctat   1800
gtgaagcttg ttgccgtagt ggtggcccga cttattgtct gaaatttttg tttcaatata   1860
tttttggtcc tcgaagctca aattttgaag tctccccatg ttttcaaata aaatagagt    1920
accttcaaaa aaaaaaaaaa aaaaaaaaaa aa                                  1952
```

<210> SEQ ID NO 6
<211> LENGTH: 1925
<212> TYPE: DNA
<213> ORGANISM: Rattus norvegicus

<400> SEQUENCE: 6

```
cagtgggcag aggctgtgag tccccgataa agagagcgcc taacatttcc gtggtattcc     60
catttgctag tgcgctgctg cggccacacg cctgattgat atatgcctgc aatggcactt    120
ttccatttga cactctccct ctctctccct ctccctctct ctccctctct ctctctccct    180
ctctctccct gggtcgctta aacaacagtc ctaacttttg tgtgttgcaa atataaaagg    240
caagccatgt gacagaggga cagaagaaca aaagcatttg gaagtaacag gacctctttc    300
tagctctcag aaaagtctga gaagaaagga gccctgcgtt tccccaagc tgtgtagcag     360
gcactgcggt gatggtgatc ggttgcaagt gaaagaagca agacaaactc ctgcatacaa    420
aggacaatga caaccagaaa acggcagccc catcctgccc tggccttgaa agggattgga    480
tcctaggagg tggcagcatt tcagatctat tgtcctctgt cgccctctgc tgttcttctg    540
gagaagtttc cccttacaac aatgagaaat catgtactag ctgcatccat ttctatgctc    600
tccctgctgg ccataatggg agatacgac agcaaaacag acagctcgtt cctgatggac     660
tctcaacgct gcatgaggca ccattatgtc gattctatca gtcacccatt gtacaaatgt    720
agctcaaaga tggtgctcct ggccagatgt gaggggcact gcagccaggc atcacgctct    780
gaacccttgg tgtccttcag cactgtcctc aagcaacctt tccgttcctc ctgtcactgc    840
tgccgacccc agacttccaa gctgaaggct ctgcgtctgc gttgctcagg gggcatgcga    900
cttactgcca cttaccggta catcctctcc tgtcactgtg aggaatgcag ctcctgaggc    960
ttgctgatga ttggctttct ggctggcaca accacaggag caattcaacc tgctagagaa   1020
```

```
ggactggcaa gaaaagagtt aaggcagata aagatggagc aagtaccaca ggattgtgca    1080
tactctagtc ctaaagactc gatgtgcttt caacagaaag tgactctggg agcttgctct    1140 tcattcccctt ctcctttctg tggaagaatt tcttttggtt acttttcaga ttcaggcatt   1200 tcccctttg gctctgattg tggtttgggt tcctgacagc tctgtattag tgggaaaatg     1260
tggggccctg tgcaagagca cgtcaggtgg tccctatttg gtgcatatta gggaagaatt    1320
taccgaagtc tccttcagtt gttgtttccc cttgttgttt tggtctaaga tttgcctcta    1380
aaggttccca gtttcaaggt ctggacacca agtccatgga tatgtttaga gaggtttact    1440
cacagccagc taactgctac taaataacta acacacgggt tctttcatgt gacagcggga    1500
ctcctgacca ctatagttgt tattcagaaa tgacttaggg gatataaagg tggcagaagg    1560
aatttataat ctgaagactt ttgcaggtaa atgatggtaa acttttgtga ggaagcaggc    1620
tttcacacat atacactcag atggatcctg tcttggctct ggagaaggca tacattacat    1680
gtggcatgga gaacacatca tactcttgat tgagcattag tcaagcatta gtctacttgt    1740
gggtgtgcaa tagcttcagc catatcttga atgtcattcc ctaacatcca cctgtctatg    1800
tgaagtttgt tgccataatg gtggcccggc ttatcctctg aaaactttgt tttcaatata    1860
cttttagtcc ttgaagctca aattttgaat ctccccatgt tttgaaataa aaatagagta    1920
ccttc                                                                 1925
```

METHOD AND COMPOSITIONS FOR GENETIC AND RETINAL DISEASE

RELATED APPLICATIONS

This application is a continuation application that claims priority benefit to U.S. Utility application Ser. No. 12/381,777 filed Mar. 17, 2009, now U.S. Pat. No. 9,114,078 issued Aug. 25, 2015; the contents of which are hereby incorporated by reference.

FIELD OF THE INVENTION

The subject invention relates generally to methods and therapies for the treatment of ocular diseases due to acquired retinal or vascular degeneration or genetic abnormality. More specifically, the subject invention relates to treatments and therapeutics to promote vascular and neuronal growth or differentiation in the retinal bed. Most specifically, the subject invention relates to methods and compositions for treatment of Norrie disease, familial exudative vitreoretinopathy, or other related genetic and acquired vitreoretinal and vascular developmental diseases.

BACKGROUND OF THE INVENTION

Proper vascular modeling in the retina is essential for ocular development and visual acuity. Abnormal vessel growth during development or in adulthood produces several relatively common diseases such as retinopathy of prematurity, diabetic retinopathy, and age-related macular degeneration. Normal retinal development occurs through vessels forming at the optic nerve head and spreading over the retina to form a dense network. Connolly, S E, et al, *Microvasc Res,* 1988; 36:275-290; Provis, J M, *Prog Retin Eye Res,* 2001; 20:799-821; Fruttiger, M, *Invest Ophthalmol Vis Sci,* 2002; 43:522-527. Development proceeds through formation of primary vessels along the surface of the developing retina from which divergent vessels begin to extend into the capillary beds that form the outer and inner plexiform layers of the retina. Connolly, 1988; Provis, 2001, Fruttiger, 2002. Vascular development is mediated by a series of growth factors that direct formation and extension of new vessels. Retinal development is unique in the concentration and types of signaling mediators employed to promote angiogenic sprouting from the primary vascular network and the formation of the final capillary architecture. Ohlmann, A, et al, *J Neurosci,* 2005; 25:1701-1710. One factor hypothesized to be involved in formation of primary retinal vasculature and retinal capillaries is the protein Norrin. Norrin, is a 131 amino acid long protein that is secreted into the extracellular space. Meitinger, T, et al, *Nat Genet,* 1993; 5:376-380; Berger, W, et al, *Hum Mol Genet,* 1996; 5:51-59. Two primary domains define the general Norrin protein structure: a signal peptide directs localization of the molecule; and a cysteine-knot motif provides the tertiary confirmation required for receptor binding and activation of signal transduction.

The importance of the cysteine knot-motif is highlighted by computer modeling that demonstrates the requirement of disulfide bonds between the cysteine residues in forming the structural confirmation of Norrin. Mutation(s) of the cysteine residues reduces the affinity of Norrin for its receptor and prevents activation of subsequent signaling pathways. Mutations in these residues also result in severe retinal dysgenesis and Norrie disease. However, mutations in regions other than the cysteine knot-motif produce incomplete protein folding and result in familial exudative vitreoretinopathy (FEVR) and related vitreoretinopathies (Retinopathy of Prematurity, persistent fetal vasculature).

Norrin is a ligand for the Frizzled receptor subtype 4 (Fz4). Norrin binds Fz4 with nanomolar affinity and stimulates a Wnt receptor:β-catenin signal transduction pathway that regulates retinal development and is necessary for regression of hyaloid vessels in the eye. Xu, Q, et al, *Cell,* 2004; 116:883-895; Clevers, H, *Curr Biol,* 2004; 14:R436-437; Nichrs, C, *Dev Cell,* 2004; 6:453-454. Norrin interaction with Fz4 is dependent on the cell surface receptor LRP5. Xu, 2004. Frizzled receptors are coupled to the β-catenin canonical signaling pathway that functions by the activation of Wnt target genes. Wnt protein binding to Frizzled and LRP5 inactivates glycogen synthase kinase (GSK) 3β and Axin. The inactivation of these proteins stabilizes β-catenin, which subsequently accumulates in the cell nucleus and activates the transduction of target genes that are crucial in the G1-S-phase transition, such as cyclin D1 or c-Myc. Willert K, and Nusse R, *Curr Opin Genet Dev,* 1998: 8:95-102. These pathways promote stimulation and proliferation of retinal stem cells. Inoue, T, et al, *Stein Cells,* 2006; 24:95-104.

Norrin is encoded by the NDP gene present on chromosome X at position 11.4. The importance of this gene product is highlighted by observations that inactivating mutations lead to Norrie disease which is characterized by ocular and cochlear vascular defects. Rhem, H L, et al, *J Neurosci,* 2002; 22:4286-4292; Black, G C, et al, *Hum Mol Genet,* 1999; 8:2031-2035. Silencing of the NDP gene produces incomplete regression of the primary hyaloid system and abnormal retinal maturation.

Observations that abnormalities in the Fz4 and LRP5 receptors that result in the phenotypically similar condition, FEVR underscore the importance of Norrin signaling. Robitaille, J, et al, *Nature Genet,* 2002; 32:326-330; Kondo, H, et al, *Br J Opthalnol,* 2003; 87:1291-1295; Toomes, C, et al, *Am J Hum Genet,* 2004; 74:721-730. The close association between the phenotypes produced by Norrin mutations and mutations in the Fz4 and LRP5 receptors bolsters the hypothesis that these molecules form a functional signaling group. Planutis, K, et al, *BMC Cell Biology,* 2007; 8:12.

While defects in the NDP gene and diseases due to incomplete or immature vascularization have been studied and correlated with disease, therapies presently available for Norrie disease, FEVR, or other retinal diseases are only modestly effective. Thus, there exists a need for improved therapeutics and methods of treatment for vitreoretinal disease and vascular disease in the retina.

SUMMARY OF THE INVENTION

The present invention provides a method of altering or maintaining physiological activity that involves administering a Norrin compound to a subject and measuring at least one parameter indicative of physiological activity in said subject. The physiological activity is optionally vascularization, cell proliferation, cellular interaction, neuroprotection, growth, vascular regression, b-wave response, cell viability, or substantial oscillatory potential.

The inventive process optionally includes administering a cell to the subject. The cell is optionally transfected with a nucleotide sequence encoding a Norrin compound, and administering the transfected cell to the subject. The cell is optionally a stem cell.

Numerous methods of administration are operable in the inventive methods illustratively including: systemic administration, local administration, injection, topical administration, intraocular, and iontophoretic delivery.

The inventive methods illustratively include administration of the compound to a subject. A subject is illustratively a mammal, human, cow, horse, sheep, pig, goat, chicken, cat, dog, mouse, guinea pig, hamster, rabbit, rat, and a cell.

The inventive method is preferably used to treat a subject with a pathological condition of the retina or is at risk of developing a pathological condition or the retina. The pathological condition is preferably caused by lacking a protein or a mutant protein, or by an acquired degeneration or disease of the retina requiring proliferation of progenitor cells. The pathological condition is optionally vitreoretinopathy, retinopathy of prematurity, familial exudative vitreoretinopathy, Norrie disease, persistent fetal vasculature, and macular degeneration.

The compound of the subject inventive methods is optionally recombinant. The compound further optionally has a marker. The marker is optionally green fluorescent protein, luciferase, and/or β-galactosidase.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
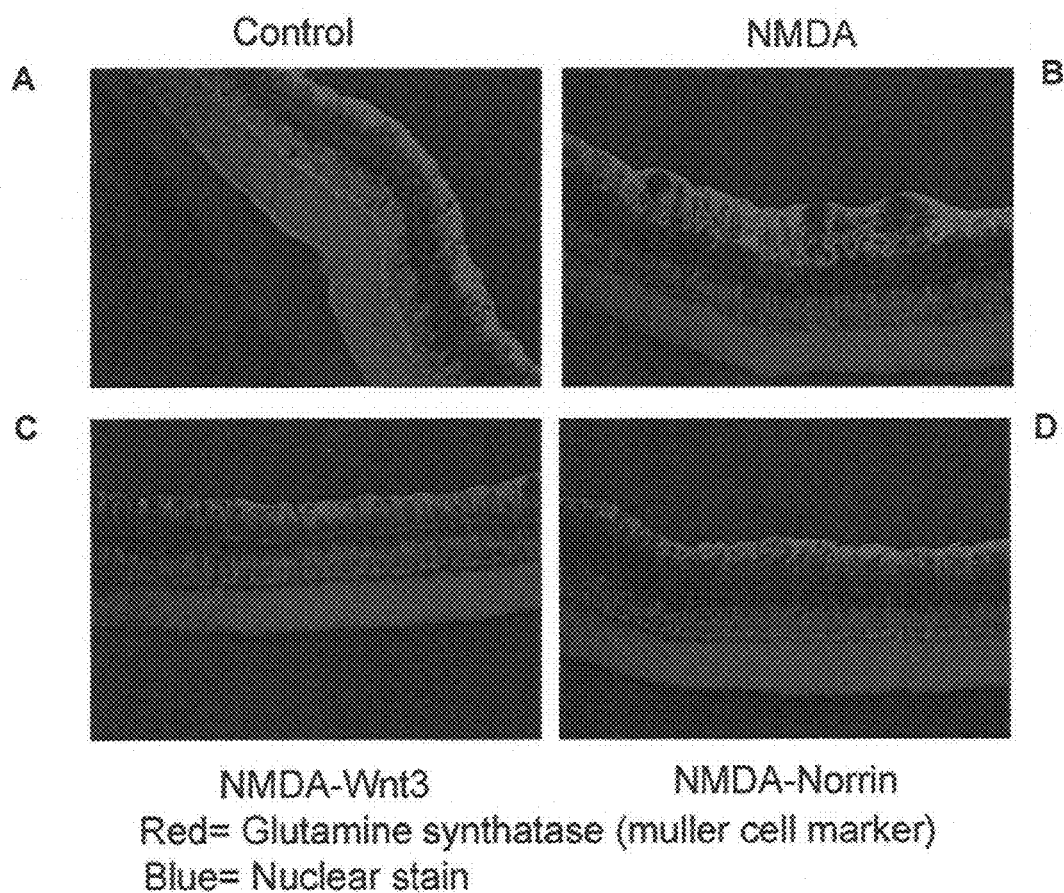
FIG. 1 depicts protection against retinal damage by NDMA in vivo.

It is to be understood that the present invention is not limited to particular embodiments described, as such may, of course, vary. It is also to be understood that the terminology used herein is for the purpose of describing particular embodiments only, and is not intended to be limiting.

A method for treatment of degenerative or inherited ocular diseases is provided. Also provided are therapeutics for the treatment of vascular diseases. Thus, the subject invention has utility for the prevention, reversal, or treatment of vitreoretinal and vascular disease.

As used herein, the term subject illustratively includes a mammal, human, cow, horse, sheep, pig, goat, chicken, cat, dog, mouse, guinea pig, hamster, rabbit, rat, a cell, tissue, organ, organ system, or combinations thereof. It is appreciated that the term subject is optionally a patient.

As used herein, the terms pathological condition or disease illustratively include vitreoretinopathy, retinopathy of prematurity (retrolental fibroplasias), Familial Exudative Vitreoretinopathy (FEVR), Norrie disease, Persistent Fetal Vasculature Syndrome (persistent hyperplastic primary vitreous), Coats disease, Macular Degeneration, Macular Dystrophy, inherited dystrophy, cancer, growth of abnormal cells, Osteoporosis-Pseudoglioma Syndrome, Non-Exudative Age Related Macular Degeneration (ARMD), Exudative Age Related Macular Degeneration (ARMD), Choroidal Neovascularization, Diabetic Retinopathy, Retinal Vein Occlussion, Retinal Artery Occlussion, Acute Macular Neuroretinopathy, Central Serous Chorioretinopathy, Cystoid Macular Edema, Diabetic Macular Edema, Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpignous Choroiditis, Subretinal Fibrosis and Uveitis Syndrome, Vogt-Koyanagi-Harada Syndrome, Parafoveal Telangiectasis, Papillophlebitis, Frosted Branch Angitis, Sickle Cell Retinopathy and other Hemoglobinopathies, Angioid Streaks, Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy, Proliferative Vitreal Retinopathy and Epiretinal Membranes, Proliferative Diabetic Retinopathy, Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associated with HIV Infection, Uveitic Disease associated with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis, Systemic Disorders with Associated Retinal Dystrophies, Congenital Stationary Night Blindness, Cone Dystrophies, Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum, Osler Weber syndrome, Retinal Detachment, Macular Hole, Giant Retinal Tear, Retinal Disease Associated with Tumors, Solid Tumors, Tumor Metastasis, Benign Tumors, for example, hemangiomas, neurofibromas, trachomas, and pyogenic granulomas, Congenital Hypertrophy of the RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors, Punctate Inner Choroidopathy, Acute Posterior Multifocal Placoid Pigment Epitheliopathy, Myopic Retinal Degeneration, Acute Retinal Pigment Epithelitis, Ocular inflammatory and immune disorders, ocular vascular malfunctions, Corneal Graft Rejection, Neovascular Glaucoma, and other diseases of ocular vascular development.

As used herein, the term physiological activity illustratively includes vascularization, cell proliferation, cellular interaction, cellular differentiation, reduction in apoptosis, reduction in necrosis, neuroprotection, growth, vascular regression, CAMKII phosphorylation, protein kinase C (PKC) activation, protein kinase A activation, activation of the MAPK pathway (illustratively, MAPK8 or JNK), downstream gene activation, activation of the β-catenin pathway, cellular viability, proteolytic activity, phosphorylation, dephosphorylation, receptor activation, receptor inactivation, other activities illustratively describe by Lin, S, et al, *Molecular Vision* 2009; 15:26-37, or combinations thereof.

As used herein, the term cell illustratively includes a somatic cell, a germ cell, a progenitor cell, a cultured cell, a stem cell, a transfected cell, or combinations thereof.

As used herein, the term administering illustratively includes delivery of a molecule or a cell to a subject by a route illustratively including systemic administration, local administration, injection, intravitreal injection, subconjuctival injection, sub-tenon injection, retrobulbar injection, suprachoroidal injection, surgical implantation, topical administration, iontophoretic delivery, oral, rectal, parenteral, intravenous, intramuscular, subcutaneous, intracisternal, intravaginal, intraperitoneal, intravesical, intraventricular, intracranial, intratumoral, local, transdermal, intrabuccal, intranasal, intrathecal, modifications thereof, or combinations thereof.

As used herein a compound is illustratively a protein, DNA, RNA, lipid, steroid, growth factor, antibody, antibody fragment, Fab', F(ab)$_2$, Fabc, Fv fragment, organic molecule, a cell, fragments thereof, mutations thereof, or mimics thereof. A compound is optionally recombinant. Most preferably, a compound encodes Norrin such as a Norrin compound.

As used herein, the term stem cell is illustratively a cell possessing self-replicating potential and the ability to give rise to terminally differentiated cells of single or multiple lineages. Stem cells are capable of generating identical progeny through unlimited numbers of cell divisions while retaining the ability to respond to physiological demands by producing daughters committed to differentiate.

Antibodies useful in the present systems include antibody fragments, such as Fab', F(ab)$_2$, Fabc, and Fv fragments. Antibody fragments are optionally produced by modification of whole antibodies or synthesized de novo using recombinant DNA methodologies, and further include "humanized" antibodies made by conventional or nonconventional techniques.

A compound administered herein is optionally supplemented with one or more agents effective in reducing inflammation, reducing pain, reducing or preventing tumor growth, reducing intraocular pressure, protecting cells, such as retinal neurons, reducing excitotoxicity, reducing infection, and reducing hemorrhage. A co-administered agent is optionally cytotoxic depending on the condition being treated. In addition, a co-administered agent optionally comprises a neurotoxic macromolecule, such as a botulinum neurotoxin, in combination with the non-neurotoxic macromolecule. A co-administered agent optionally comprises a small chemical compound in combination with the present macromolecules. Examples of chemical compounds operable herein illustratively include a small chemical compound, such as anecortave acetate, ketorlac tromethamine (such as Acular), gatifloxacin, ofloxacin, epinastine, and the like.

Optionally, a compound is delivered to a subject conjugated to a magnetic particle as described in U.S. Patent Application Publication 2004/0086572 which is incorporated herein.

A Norrin compound is illustratively a nucleotide sequence or a protein sequence encoding a Norrin protein, a fragment thereof, or a mimetic thereof. A Norrin compound is illustratively SEQ ID NOs: 1-6. A Norrin compound is optionally purified.

In a preferred embodiment Norrin protein is administered to a subject. Norrin is optionally purified from a subject or expressed in a recombinant cell system and subsequently purified. Purification is not absolutely required but is preferred. Norrin protein sequence operable herein illustratively includes that derived from human, mouse, rat, dog, cat, or other suitable organism. SEQ ID NO: 1 represents the Norrin sequence from *homo sapiens*. SEQ ID NO: 2 represents the Norrin sequence from Mus musclus. SEQ ID NO: 3 represents the Norrin sequence from *Rattus norvegicus*.

Norrin protein is optionally administered as an oligomeric complex. See Perez-Vilar, J and Hill, R L, *J Biol Chem*, 1997; 272: 33410-33415. Oligomers operable herein are optionally dimers, trimers, quadramers, pentamers, hexamers, octamers, or higher order multimers. Oligomeric complexes are optionally homomultimeric or heteromultimeric. The range of oligomeric association is preferably between monomers and 30-mers. More preferably, the oligomeric association is between dimers and 20-mers. Most preferably, the oligomeric association is monomers or dimers.

Norrin is optionally administered to a subject with a cofactor. A cofactor is illustratively a polyanion. More preferably a cofactor is heparin or heparin sulfate. It is appreciated that other polyanions or modifications thereof are similarly operable.

Norrin protein is preferably administered to a subject at a concentration suitable to alter or maintain a physiological activity. The total quantity or concentration of Norrin protein delivered is optionally dependent on the age or size of the subject as appreciated by one of skill in the art.

In a preferred embodiment a compound is a biologically active polypeptide fragment of Norrin protein which is administered to a subject. A biologically active polypeptide fragment illustratively includes residues 20-133 of SEQ ID NO: 1, Residues 30-133 of SEQ ID NO: 1, or any other truncation N-terminal to cysteine 39 of SEQ ID NO: 1 and extending toward the C-terminus of Norrin protein. It is appreciated that other polypeptide regions of the Norrin protein or nucleotide sequence will be similarly operable.

A biologically active peptide optionally is a mutant form of Norrin. Norrin mutants operable herein illustratively include amino acid substitutions relative to SEQ ID NO: 1 of R64E. Optionally the biologically active peptide is a multiple mutant relative to SEQ ID NO: 1: T27A, S28A, S29A; P36A, R37A, R38A; Y120A, R121A, Y122A; or H127A, E129A, E130A; or combinations thereof. Any amino acid mutated in a multiple mutation is operable as a single mutation. Other sequence mutations operative herein are illustrated in FIG. 6A of Smallwood, P M, et al, *J Biol Chem*, 2007: 282:4057-4068. It is appreciated that other mutations at different amino acid sites are similarly operable. It is further appreciated that mutation of the conserved amino acid at any particular site is preferably mutated to glycine or alanine. It is further appreciated that mutation to any neutrally charged, charged, hydrophobic, hydrophilic, synthetic, non-natural, non-human, or other amino acid is similarly operable.

Modifications and changes are optionally made in the structure (primary, secondary, or tertiary) of the Norrin protein which are encompassed within the inventive compound that may or may not result in a molecule having similar characteristics to the exemplary polypeptides disclosed herein. It is appreciated that changes in conserved amino acid bases are most likely to impact the activity of the resultant protein. However, it is further appreciated that changes in amino acids operable for receptor interaction, resistance or promotion of protein degradation, intracellular or extracellular trafficking, secretion, protein-protein interaction, post-translational modification such as glycosylation, phosphorylation, sulfation, and the like, may result in increased or decreased activity of an inventive compound while retaining some ability to alter or maintain a physiological activity. Certain amino acid substitutions for other amino acids in a sequence are known to occur without appreciable loss of activity.

In making such changes, the hydropathic index of amino acids are considered. According to the present invention, certain amino acids can be substituted for other amino acids having a similar hydropathic index and still result in a polypeptide with similar biological activity. Each amino acid is assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Without intending to be limited to a particular theory, it is believed that the relative hydropathic character of the amino acid determines the secondary structure of the resultant polypeptide, which in turn defines the interaction of the polypeptide with other molecules. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gin, His), (Asp: Glu, Cys, Ser), (Gin: Asn), (Glu: Asp), (Gly: Ala), (His: Asn, Gin), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

In a preferred embodiment a compound is a Norrin mimetic. A Norrin mimetic is illustratively a polypeptide, lipid, DNA structure, RNA structure, small molecule, other molecule optionally capable of interacting with a Fz receptor, fragments thereof, synthetic analogous thereof, or combinations thereof. Preferably a Norrin mimetic is a molecule capable of stimulating signaling via the Fz4 receptor. Norrin mimetics operable herein are illustratively a WNT protein, a mutation of a WNT protein, antibodies, antibody fragments, or combinations thereof. It is appreciated that other molecules known in the art to stimulate signaling via Fz4 are similarly operable.

Multiple physiological activities are altered or maintained in the present inventive method. Physiological activities illustratively include vascularization, cell proliferation, cellular interaction, neuroprotection, growth, vascular regression, b-wave response, substantial oscillatory potential, or combinations thereof.

In a preferred embodiment Norrin is administered to a subject as a factor suitable for expression within the eye or within a cell located in the eye. An exemplary system for the expression of protein is described in U.S. Patent Application Publication 2003/0129164, which is incorporated herein by reference with particularity for disclosure of diseases, gene delivery methods, and gene expression methods. Any of a variety of vectors adapted for expression of Norrin in a cell of the eye, preferably within a retinal cell, are within the scope of the present invention. Gene delivery vectors are optionally viral (e.g., derived from or containing sequences of viral DNA or RNA, preferably packaged within a viral particle), or non-viral (e.g., not packaged within a viral particle, including "naked" polynucleotides, nucleic acid associated with a carrier particle such as a liposome or targeting molecule, and the like).

The viral factor operable herein is illustratively a recombinant adeno-associated viral (rAAV) vector. It is appreciated the other suitable vectors known in the art are similarly operative. Additional illustrative vectors optionally include adenoviral vectors, alphaviral vectors, viruses illustratively including pox viruses-illustratively canary pox virus or vaccinia virus, SV40, influenza virus, HIV, herpes, measles, Semliki Forest Virus, and coronavirus, as well as other viral systems. In addition, viral carriers are optionally homologous, non-pathogenic (defective), replication competent virus.

A particularly preferred gene delivery vector is a rAAV vector. A variety of rAAV vectors are optionally utilized to direct the expression of a neurotrophic factor such as Norrin. An operable rAAV is generally comprised of, in order of 5' to 3', a 5' adeno-associated virus inverted terminal repeat, a coding sequence for the desired gene product (e.g., Norrin) operatively linked to a sequence which regulates its expression in a cell (e.g., a promoter sequence), and a 3' adeno-associated virus inverted terminal repeat. A promoter sequence is preferably a cell specific promoter sequence. In addition, the rAAV vector preferably has a polyadenylation sequence. The promoter is illustratively a constitutive promoter, a cell specific promoter, a selective molecule responsive promoter, or combinations thereof. Preferably a promoter is a cell specific promoter. More preferably, a promoter is a constitutive promoter that is cell type specific. Promoter sequences operative herein illustratively include the GFAP promoter, a retinal pigment cell specific promoter, a Muller cell specific promoter, promoters described in WO/2000/015822, which is incorporated herein by reference, a Cdc6 promoter, human ICAM-2 promoter, promoters and vectors described by Dai, C, et al, *J Virology,* 2004; 78:6209-6221, or other promoter known in the art.

Norrin is optionally delivered to the eye by one or multiple routes illustratively including intraocularly, by topical application to the eye or by intraocular injection illustratively into the vitreous or subretinal (interphotoreceptor) space. Alternatively, delivery is local by insertion or injection into the tissue surrounding the eye, systemically through an oral route, or by subcutaneous, intravenous or intramuscular injection. Alternatively, delivery is by a catheter or by means of an implant, wherein such an implant is made of a porous, non-porous or gelatinous material, including membranes such as silastic membranes or fibers, biodegradable polymers, or proteinaceous material. A compound is illustratively administered prior to the onset of a pathological condition to prevent its occurrence, for example, during or prior to surgery on the eye, or immediately after the onset of the pathological condition or during the occurrence of an acute or protracted disease.

In a preferred embodiment, a compound is administered to the eye, preferably intraocularly to a variety of locations within the eye depending on the type of disease to be treated, prevented, or, inhibited, and the extent of disease. Examples of suitable locations include the retina (e.g., for retinal diseases), the vitreous, or other locations in or adjacent the retina or in or adjacent to the eye.

In a preferred embodiment a cell is transfected with a nucleotide sequence encoding a Norrin protein, a biologically active fragment of a Norrin protein, or a Norrin mimetic. Preferably, a nucleotide sequence is cloned into an expression vector with a promoter. The promoter is illustratively a constitutive promoter, strong promoter (e.g., CMV promoters), inducible promoter, tissue-specific promoter, a cell specific promoter, a selective molecule responsive promoter, or combinations thereof. Preferably a promoter is a cell specific promoter. More preferably, a promoter is a constitutive promoter that is cell type specific. Promoter sequences operative herein illustratively include the GFAP promoter, a retinal pigment cell specific promoter, a Muller cell specific promoter, promoters described in WO/2000/015822, which is incorporated herein by reference, a Cdc6 promoter, human ICAM-2 promoter, promoters and vectors described by Dai, C, et al, *J Virology*, 2004; 78:6209-6221, or other promoter known in the art. In a preferred embodiment a tetracycline responsive promoter is used to limit expression to instances when tetracycline is present in the system.

Numerous enhancers are operable to stimulate expression of Norrin in a transfected cell. Illustratively an endothelial enhancer such as that described by Shaw, L C, et al, *Gene Therapy*, 2006; 13:752-760 is operative herein.

A cell is preferably a mammalian cell. A cell is optionally an endothelial cell, vascular cell, stem cell, immortalized cell, or combinations thereof. Preferably, a cell is a stem cell. It is appreciated that a stem cell illustratively includes a primary stem cells and lineage cells.

In a preferred embodiment, the cell is a stem cell. A stem cell operable herein and its method of isolation and preparation is illustratively described in U.S. Patent Application Publication 2007/0154465 A1, which is incorporated herein by reference. Stem cells are illustratively transfected with a vector encoding and inventive compound. Suitable vectors and methods of administration to a stem cell are also illustrated in U.S. Patent Application Publication 2007/0154465 A1. Stem cells are optionally transiently transfected or transfected with a vector that provides incorporation into the host genome and constitutive expression.

In a preferred embodiment, a cell is transfected with an expression vector encoding a Norrin protein, a biologically active peptide fragment of a Norrin protein, or a Norrin mimetic and the transfected cell is administered to a subject. An advantage to this embodiment is that possible barriers to optimal protein expression from host cells are overcome by capitalizing on known techniques of in vitro cell transfection. As such, delivery of Norrin protein to the retina of a subject is greatly simplified and expression is improved or maximized. Further, when endothelial cell, stem cell capable of differentiating into an endothelial cell, or other suitable cell type is used as the transfected cell, its subsequent administration to the eye of a subject provides suitable endogenous growth mediators such that cell survival is optimal and duration of successful delivery of a compound is maximized in concentration and time.

Optionally, a cell is derived from a patient. Illustratively, a stem cell is obtained from the patient, transfected, and administered to the patient as a Norrin expressing cell. In a preferred embodiment a retinal cell is obtained from a subject, is transfected with an expression vector expressing an inventive compound, and the transfected cell is administered to the subject.

Administration to the ocular environment in a subject is most preferably by injection into the vitreous. While patients who suffer from a pathological condition of the retina are amenable to multiple injections over the course of time, the use of transfected cells expressing a compound will preferably reduce the number of injections a subject must endure. Illustratively, a single injection of endothelial cells that have been transfected with a vector expressing an inventive compound onto the retina of a subject provides a long-term delivery of the inventive compound to the subject's retina. As such, a single therapeutic delivery will produce a clinical benefit.

In a most preferred embodiment the instant inventive method is employed with a subject that has a pathological condition. Pathological conditions are preferably vitreoretinopathy, retinopathy of prematurity, familial exudative vitreoretinopathy, Norrie disease, persistent fetal vasculature syndrome, Coats disease, macular degeneration, macular dystrophy, inherited dystrophy, cancer, growth of abnormal cells, osteoporosis-pseudoglioma syndrome, and other diseases of ocular vascular and retinal development.

Preferably, a pathological condition results from, is caused by, is related to, or otherwise is associated with a mutation in the NDP gene, alteration in transcription to mRNA. mRNA survival, mRNA degradation, alternative mRNA splicing, protein translation, protein survival, protein degradation, protein trafficking, expression of protein on a cell membrane, protein secretion, or other abnormality in production of a functional Norrin protein. This includes decreased production of Norrin secondary to alternate gene expression or suppressed gene activation, seen in mature tissues. Most preferably, a pathological condition is associated with a mutation in the Norrin protein. In a most preferred embodiment a pathological condition is a pathological condition of the retina.

In a most preferred embodiment a compound is administered to a subject with a pathological condition and the presence of the compound alters or maintains at least one physiological activity. A physiological activity is preferably observed in the retina of a subject. This embodiment has the greatest efficacy in patients suffering from diseases that manifest themselves during development and childhood such as FEVR or Norrie disease. Further, patients illustratively presenting with age related macular degeneration or young patients presenting with early stage disease will benefit from maintenance of retinal vascularization, oxygenation, or visual acuity. The instant inventive method is operable to reduce the rate of visual or other vascular related degeneration relative to subjects not receiving treatment.

A function of the retina is illustratively vascularization, cell proliferation, cellular interaction, neuroprotection, growth, vascular regression, b-wave response, substantial oscillatory potential, Wnt signaling, Fz signaling, CAMKII autophosphorylation, PKC activation, protein kinase A activation, activation of the MAPK pathway, stimulation of gene transcription, activation of intracellular signaling pathways illustratively including the PI3K/Akt pathway, preventing nuclear translocation of c-Jun N-terminal protein (JNK), or regulating caspase activation, stimulation of marker signaling, inhibition of marker signaling, maintenance of marker signaling, or combinations thereof. In a preferred embodiment retinal vascularization is increased. Most preferably, retinal vascularization approaches that observed in subjects that do not present with a pathological condition of the retina. It is appreciated that other markers of proper vascularization are also a function of the retina.

These illustratively include development or differentiation of neuronal cells, or activity of neuronal cells.

A marker is illustratively a component of a compound. Illustratively, a cell is transfected with an expression vector that encodes a marker as well as a vector that encodes a compound. The administration of a marker provides the advantage of monitoring the function of the inventive method in cells or in a subject to whom a compound is administered. Markers operable herein are illustratively green fluorescent protein, luciferase, and 3-galactosidase. It is appreciated that other suitable markers known in the art are similarly operable. A marker is optionally radioactive, luminescent, biologically active, or otherwise amenable to detection by methods known in the art.

Methods involving conventional biological techniques are described herein. Such techniques are generally known in the art and are described in detail in methodology treatises such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Various aspects of the present invention are illustrated by the following non-limiting examples. The examples are for illustrative purposes and are not a limitation on any practice of the present invention. It will be understood that variations and modifications can be made without departing from the spirit and scope of the invention. While the examples are generally directed to mammalian tissue, specifically, analyses of murine tissue, a person having ordinary skill in the art recognizes that similar techniques and other techniques known in the art readily translate the examples to other organisms such as humans. Reagents illustrated herein are commonly cross reactive between mammalian species or alternative reagents with similar properties are commercially available, and a person of ordinary skill in the art readily understands where such reagents may be obtained.

Example 1

Preparation of Norrin containing microspheres. Norrin purchased from R&D Systems, Minneapolis, Minn., or cloned, expressed and purified is loaded into biodegradable microspheres substantially as described by Jiang, C, et al, *Mol Vis,* 2007; 13:1783-92 using the spontaneous emulsification technique of Fu, K, et al, *J Pharm Sci,* 2003; 92:1582-91. Microspheres are synthesized and loaded by dissolving 200 mg of 50:50 PLGA (DURECT Corp., Birmingham, Ala.) in 5 ml of 4:1 volume ratio trifluoroethanol: dichloromethane supplemented with 8 mg magnesium hydroxide to minimize protein aggregation during encapsulation. 10 µg Norrin is reconstituted in 300 µl 7 mg bovine serum albumin (BSA) and 100 mg docusate sodium (Sigma-Aldrich, St. Louis, Mo.) dissolved in 3 ml PBS. The solution is vortexed and poured into 200 ml of 1% (w/v) polyvinyl alcohol (PVA, 88% hydrolyzed) with gentle stirring. Microspheres are hardened by stirring for three hours, collected by centrifugation, and washed three times to remove residual PVA. If the microspheres are not to be immediately injected they are rapidly frozen in liquid nitrogen, lyophilized for 72 h, and stored in a dessicator at −20° C. Norrin containing microspheres exhibit average diameters of 8 µm as determined by a particle size.

Example 2

Intravitreal injection of Norrin. Norrin in solution, packaged into microspheres as described in Example 1, or expressed in cells, or in purified form in solution is exposed to the retina by intravitreal injection substantially as described by Jiang, 2007. Intravitreal injection is performed under general anesthesia using an ophthalmic operating microscope (Möller-Wedel GmbH, Wedel, Germany) using beveled glass micro-needles with an outer diameter of approximately 100 µm. Microsphere suspensions are prepared in PBS at 2 and 10% (w/v) and briefly vortexed immediately before injection to ensure a uniform dispersion. A 30-gauge hypodermic needle is used to perfbrate the sclera 1.5 mm behind the limbus. Five µl of test sample is optionally injected by way of this passage into the vitreous using a 50 µl Hamilton Syringe (Hamilton Co, Reno, Nev.). To ensure adequate delivery and prevent shock the needle is held in place fbr one min after the injection is completed and subsequently withdrawn slowly. In addition, paracentesis is simultaneously performed to relieve pressure and thereby prevent reflux.

Example 3

Delivery of Norrin to the retina by a controlled release delivery system. An implantable controlled release delivery system is described in U.S. Patent Application Publication 2005/0281861 A1 which is incorporated herein by reference for its entire disclosure, figures, examples, and methods. Norrin is packaged into such as system at 100 µg per final formulated capsule. The Norrin containing drug delivery systems are placed in the eye using forceps or a trocar after making a 2-3 mm incision in the sclera. Alternatively, no incision is made and the system is placed in an eye by inserting a trocar or other delivery device directly through the eye. The removal of the device after the placement of the system in the eye can result in a self-sealing opening. One example of a device that is used to insert the implants into an eye is disclosed in U.S. Patent Application Publication No. 2004/0054374 which is incorporated herein by reference. The location of the system may influence the concentration gradients of therapeutic component or drug surrounding the element, and thus influence the release rates (e.g., an element placed closer to the edge of the vitreous may result in a slower release rate). Thus, it is preferred if the system is placed near the retinal surface or in the posterior portion of the vitreous.

Example 4

Treatment of retinal explants with Norrin. Retinal explants from rats or mice are obtained and cultured as described. Nakhai, H, et al, *Development,* 2007; 134:1151-1160. Eyes are isolated from E18.5 embryos. Explants of the neural retina are dissected and placed into a Millicell CM chamber (Millipore) with the ganglion cell layer upward and cultured in 50% DMEM (Gibco) supplemented with HEPES, 25% Hank's solution, 25% heat-inactivated horse serum, 200 µM L-glutamine and 6.75 mg/ml glucose at 34° C. in a 5% $CO_2$ incubator.

Example 5

Administered Norrin is protective of NDMA induced retinal damage. Eighteen adult male ddY mice weighing 36 to 43 g each are anesthetized with 3.0% isoflurane and maintained with 1.5% isoflurane in 70% $N_2O$ and 30% $O_2$. Body temperatures are maintained between 37.0° C. and 37.5° C. with the aid of a heating pad and a heating lamp. One eye of each animal is designated a control eye with the other eye used as a test eye. At day 0 all test eyes and ½ of control eyes are injected into the vitreous body with n-methyl D-aspartate (NMDA) (Sigma-Aldrich) at 200 nM per eye dissolved in 0.01 M phosphate-buffered saline (PBS) to induce retinal damage. The remaining control eyes are injected with an equal volume of PBS. At day 1, test eyes are injected with either Wnt3 or Norrin as prepared in example 1 at concentrations of 0.1, 1, or 10 ng per eye. One drop of levofloxacin ophthalmic solution (Santen Pharmaceuticals Co. Ltd., Osaka, Japan) is applied topically to each eye after intravitreous injection. Animals are returned to cages and maintained until day 6 at which time they are sacrificed and all eyes are enucleated for retinal tissue fixation and immunohistochemistry. Eyes are enucleated, fixed in 4% paraformaldehyde overnight at 4° C., immersed in 20% sucrose for 48 hours at 4° C., and embedded in optimum cutting temperature (OCT) compound (Sakura Finetechnical Co., Ltd., Tokyo, Japan). Transverse, 10-µm-thick cryostat sections are cut and placed onto slides (Mas Coat). Sections are subsequently processed for immunocytochemistry following staining for Glutamine synthatase and staining for DNA using DAPI.

NMDA treated eyes develop numerous lesions indicative of neuronal damage (FIG. 1B). Treatment with positive control Wnt3 illustrates much less retinal damage (FIG. 1C). Treatment of mouse eyes with norrin is protective of damage as illustrated by nearly complete protection against NMDA damage as compared to control eyes (FIG. 1D).

Example 6

Figure 2:
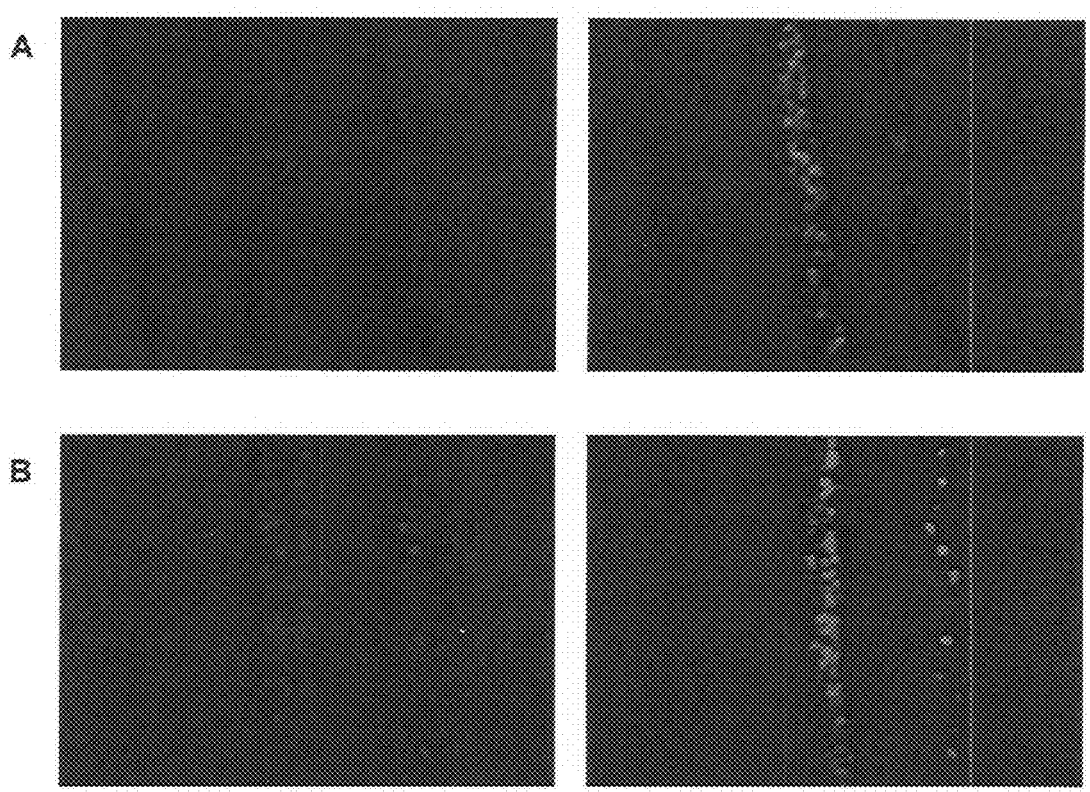
FIG. 2 depicts growth and differentiation of neural progenitor cells in vivo retinas following administration of Norrin.

Norrin promotes retinal progenitor cell differentiation in NMDA damages eyes. Mouse eyes are treated with PBS, NMDA, or NMDA plus Norrin as described in example 5. Retinal samples are stained with either Chx10 or Pax6. Co-staining with both Chx10 (red) and Pax6 (green) is indicative of the presence of retinal progenitor cells. Norrin treatment (FIG. 2B) results in increased numbers of retinal progenitor cells as compared to control non-norrin treated eyes (FIG. 2A).

Example 7

Norrin produces earlier development of vascular channels in developing stem cells.

Endothelial stem cells (EC cells) are differentiated and analyzed essentially as described by Ng, Y, et al. *Laboratory Investigation*, 2004; 84:1209-1218. Briefly, trypsinized ES cells are suspended in culture medium including high-glucose Dulbecco's modified Eagle's medium (DMEM, GIBCO BRL, Grand Island, N.Y., USA) with 15% fetal bovine serum (Hyclone, Utah, USA), sodium pyruvate (GIBCO, stock solution diluted 1:100), nonessential amino acids (GIBCO, stock solution diluted 1:100), β-mercaptoethanol (GIBCO, final concentration 30 µM), 190 µg/ml of L-glutamine, 60 U/ml of penicillin G, 60 µg/ml of streptomycin (glutamine pen-strep mix, Irvine Scientific, Santa Ana, Calif., USA), supplemented with media (1:300 dilution) conditioned by Chinese hamster ovary cells overexpressing LIF (provided by Genetics Institute, Cambridge, Mass., USA) as a source of LIF to maintain the ES cells in an undifferentiated state in a humidified tissue culture incubator at 10% $CO_2$ and 37° C., and passaged every 2-3 days. Cells are either cultured in the presence or absence of Norrin.

ES cells are differentiated into embroyid bodies A total of 60 aliquots (30 µl) of ES cell suspension containing $2.5 \times 10^3$ cells are plated as individual drops onto 100 mm² bacteriological dishes (Valmark Inc., Canada). The plates are then gently inverted into hanging drops and the cells incubated. The CEB are cultivated for 40-45 h, and then the dishes are turned right side up and flooded with 10 ml of ES culture media without LIF. The culture media is replaced every three days. The attached cultures of CEB are transferred at day 4 or day 5 to gelatin-coated tissue culture plates or gelatin-coated cover glasses, onto which the CEB attaches, flattens and spreads. Cells are fixed and stained for PECAM-1 expression as described by Ng, Y, et al.

Figure 3:
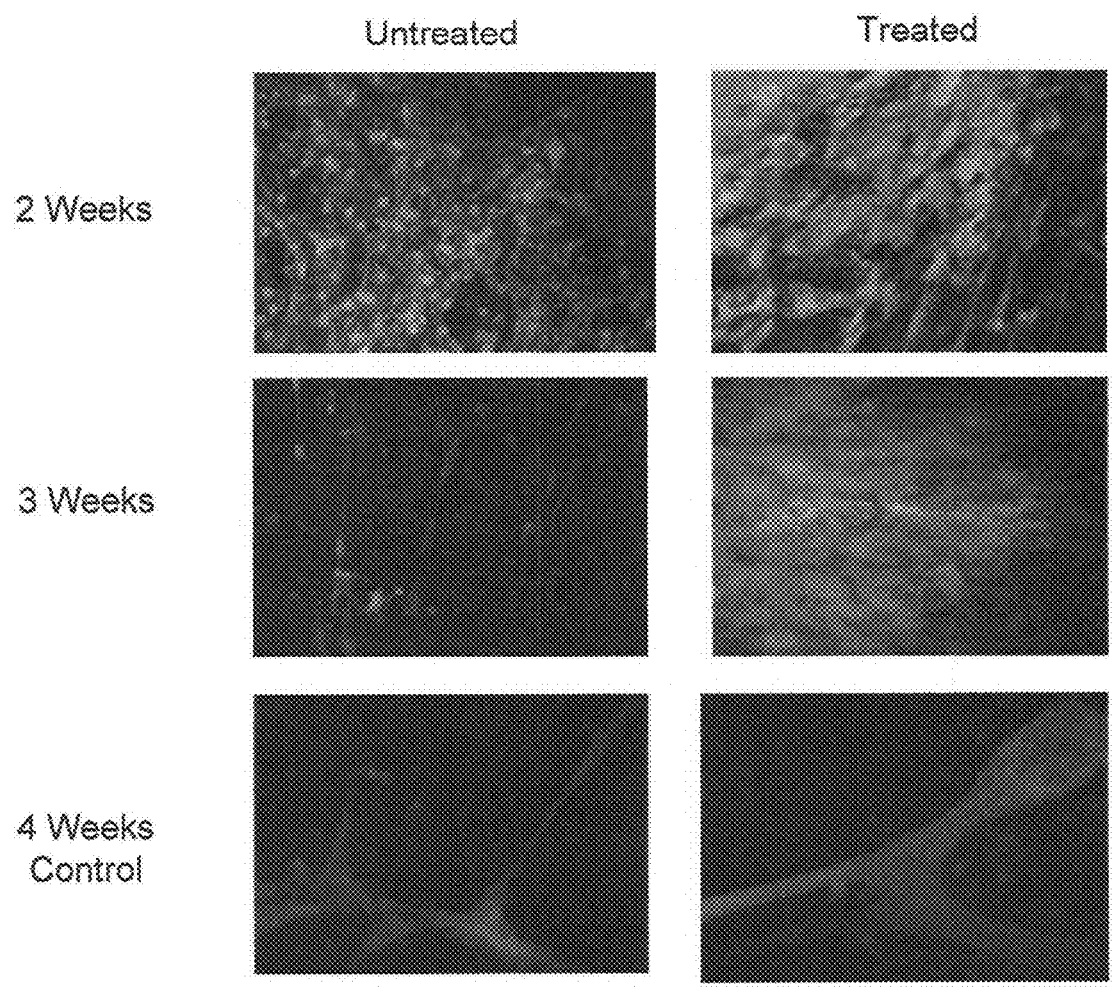
FIG. 3 depicts early development of vascular channels during development of stem cells into embroyid bodies due to the presence of Norrin.
Figure 4:
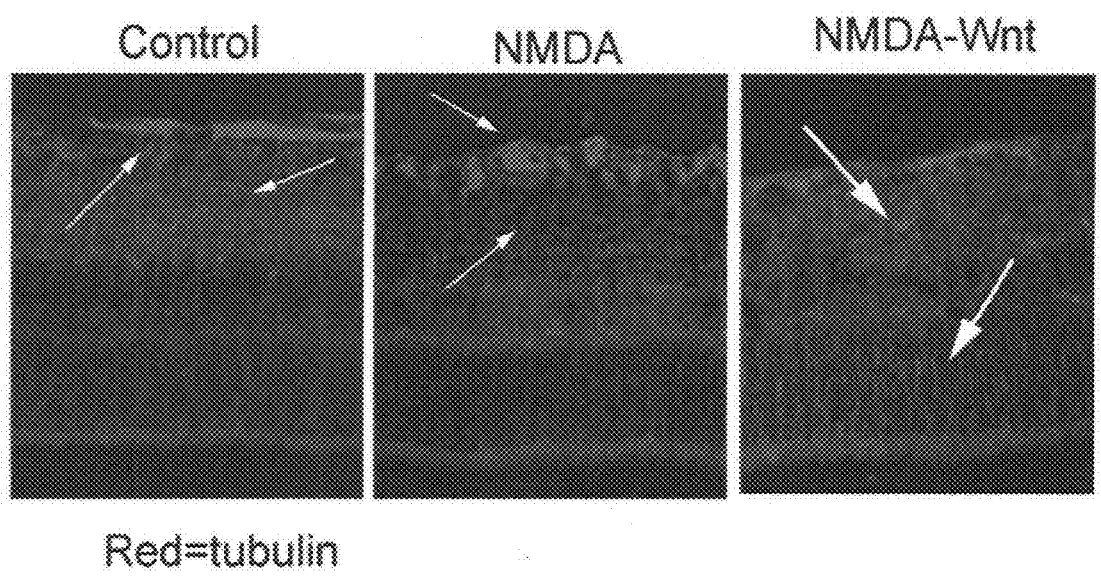
FIG. 4 depicts in vivo retinal cell differentiation and protection from NDMA damage by activation of the Wnt pathways.
Figure 5:
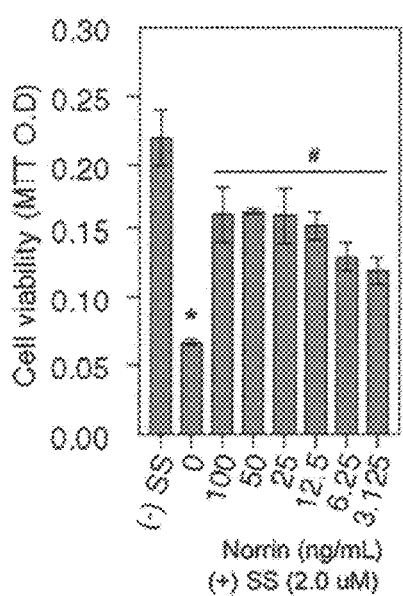
FIG. 5 depicts subsequent art illustrating protection of RGC5 cell viability from staurosporine damage by various concentrations of Norrin. Lin, S, et al, *Molecular Vision* 2009; 15:26-37, the entire contents of which are incorporated herein by reference.

PECAM-1 staining (red) reveals that Norrin induces earlier vascular channel development than non-norrin treated cells with vascular channels appearing at week 2 in Norrin treated groups and not readily apparent in untreated until week 4 (FIG. 3).

Example 8

Treatment of Norrie disease eyes with recombinant Norrin promotes improved retinal response. Subjects who have been diagnosed with Norrie disease or are at risk for Norrie disease are exposed to norrin prepared essentially as described in example 1 and administered as described in examples 2 or 3. Administration is performed either a single time, or repeated weekly depending on the delivery mechanism used. At weeks 1, 2, 4, and 20 subjects are analyzed for improved retinal physiological activity using electroretinograms by methods known in the art or illustratively as described by Wu, W, et al., *Molecular Vision*, 2004; 10:93-102. Subjects treated with Norrin demonstrate improved a- and b-wave measurements at all-time points tested.

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The following references are each incorporated herein by reference for the entirety of their contents as if each reference were fully and explicitly included.

REFERENCE LIST

1. Connolly, S E, et al, *Microvasc Res,* 1988; 36:275-290
2. Provis, J M, *Prog Retin Eye Res,* 2001; 20:799-821
3. Fruttiger, M, *Invest Ophthanol Vis Sci,* 2002; 43:522-527
4. Ohlmann, A, et al, *J Neurosci,* 2005; 25:1701-1710
5. Meitinger, T, et al, *Nat Genet,* 1993; 5:376-380
6. Berger, W, et al, *Hum Mol Genet,* 1996; 5:51-59
7. Xu, Q, et al, *Cell,* 2004; 116:883-895
8. Clevers, H, *Curr Biol,* 2004; 14:R436-437

9. Nichrs, C, *Dev Cell,* 2004; 6:453-454
10. Willert K, and Nusse R, *Curr Opin Genet Dev,* 1998; 8:95-102.
11. Inoue, T, et al, *Stem Cells,* 2006; 24:95-104
12. Rhem, H L, et al, *J Neurosci,* 2002; 22:4286-4292
13. Black, G C, et al, *Hum Mol Genet,* 1999; 8:2031-2035
14. Robitaille, J, et al, *Nature Genet,* 2002; 32:326-330
15. Kondo, H, et al, *Br J Opthanol,* 2003; 87:1291-1295
16. Toomes, C, et al, *Am J Hum Genet,* 2004; 74:721-730
17. Planutis, K, et al *BMC Cell Biology,* 2007; 8:12
18. Perez-Vilar, J and Hill, R L, *J Biol Chem,* 1997; 272: 33410-33415
19. Smallwood, P M, et al, *J Biol Chem,* 2007; 282:4057-4068
20. Shaw, L C, et al, *Gene Therapy,* 2006; 13:752-760
21. Dai, C, et al, *J Virology,* 2004; 78:6209-6221
22. Nakhai, H, et al, *Development,* 2007; 134:1151-1160
23. Jiang, C, et al, *Mol Vis,* 2007; 13:1783-92
24. Fu, K, et al, *J Pharm Sci,* 2003; 92:1582-91
25. Lin, S, et al, *Molecular Vision* 2009; 15:26-37

```
REFERENCE SEQUENCES
SEQ ID NO 1: Norrin (Homo sapiens)
protein sequence
    1 mrkhvlaasf smlsllvimg dtdsktdssf imdsdprrcm
      rhhyvdsish plykessskinv 61 llarceghes qasrseplvs fstvlkqpfr sschccrpqt
      sklkalrlrc sggmrltaty 121 ryilschcee ens SEQ ID NO 2: Norrin (Mus musculus)
protein sequence
    1 mrnhvlaasi smlsllaimg dtdsktdssf lmdsqrcmrh
      hyvdsishpl ykessknmll 61 arceghcsqa srseplvsfs tvlkqpfrss chccrpqtsk
      lkalrlrcsg gmrltatyry 121 ilschceecs s SEQ ID NO 3: Norrin (Rattus norvegicus)
protein sequence
    1 mrnhvlaasi smlsllaimg dtdsktdssf lmdsqrcmrh
      hyvdsishpl ykcsskmvll 61 arceghcsqa srseplvsfs tvlkqpfrss chccrpqtsk
      lkalrlrcsg gmrltatyry 121 ilschceecs s SEQ ID NO 4: NDP gene (Homo sapiens)
    1 attcccattt gctagtgcgc tgctgcggcc gcacgcctga
      ttgatatatg actgcaatgg 61 cacttttcca tttgacattc tctctctctc tctccctctc
      tctctctccc tctctctctc 121 cctctctctc tctccctgtg tcgcttaaac aacagtccta
      acttttgtgt gttgcaaata 181 taaaaggcaa gccatgtgac agagggacag aagaacaaaa
      gcatttggaa gtaacaggac 241 ctcttttctag ctctcagaaa agtcgagaa gaaaggagcc
      ctgcgttccc ctaagctgtg 301 cagcagatac tgtgatgatg gattgcaagt gcaaagagta
      agacaaaact ccagcacata 361 aaggacaatg acaaccagaa agcttcagcc cgatcctgcc
      ctttccttga acgggactgg 421 atcctaggag gtgaagccat ttccaatttt tgtcctctg
      cctccctctg ctgttcttct 481 agagaagttt ttccttacaa caatgagaaa acatgtacta
      gctgcatcct tttctatgct 541 ctccctgctg gtgataatgg gagatacaga cagtaaaacg
      gacagctcat tcataatgga 601 ctcggaccct cgacgctgca tgaggcacca ctatgtggat
      tctatcagtc acccattgta 661 caagtgtagc tcaaagatgg tgctcctggc caggtgcgag
      gggcactgca gccaggcgtc 721 acgctccgag cctttggtgt cgttcagcac tgtcctcaag
      caaccctccc gttcctcctg 781 tcactgctgc cggccccaga cttccaagct gaaggcactg
      cggctgcgat gctcaggggg 841 catgcgactc actgccacct accggtacat cctctcctgt
      cactgcgagg aatgcaattc 901 ctgaggcccg ctgctgtgtg tggcttctgg atgggacaac
      tgtagaggca gttcgaccag 961 ccagggaaag actggcaaga aaagagttaa ggcaaaaaag
      gatgcaacaa ttctcccggg 1021 actctgcata ttctagtaat aaagactcta catgcttgtt
      gacagagaga gatactctgg 1081 gaacttattt gcagttccca tctcctttct ctggtacaat
      ttcttttggt tcatttttcag 1141 attcaggcat tttccccctt ggctctcaat gctgtttggg
      tttccaacaa ttcagcatta 1201 gtgggaaaaa gtgggccctc atacacaagc gtgtcaggct
      gtcagtgttt ggtgcacgct 1261 ggggaagaat ttactttgga aagtagaaaa gcccagcttt
      tcctgggaca tcttctgtta 1321 ttgttgatgt ttttttttac cttgtcattt tggtctaagg
      ttgccattgc tgctaaaggt 1381 taccgatttc aaagtccaga taccaagcat gtggatatgt
      ttagctacgt ttactcacag 1441 ccagcgaact gacattaaaa taactaacaa acagattctt
      ttatgtgatg ctggaactct 1501 tgacagctat aattattatt cagaaatgac tttttgaaag
      taaaagcagc ataaagaatt 1561 tgtcacagga aggctgtctc agataaatta tggtaaaatt
      ttgtaaggga gcagacttttt 1621 aaagacttgc acaaatacgg atcctgcact gactctggaa
      aaggcatata tgtactagtg 1681 gcatggagaa tgcaccatac tcatgcatgc aaaattagaca
      accaagtatg aatctatttg 1741 tgggtgtgct atagctttag ccgtgtcacg ggcatcattc
      tctaatatcc acttgtccat 1801 gtgaaacatg ttgccaaaat ggtggcctgg cttgtcttct
      gaacgtttgg ttcaaatgtg 1861 ttttggtcct ggaggctcaa attttgagtt attcccacgt
      tttgaaataa aaagagtata 1921 ttcaaaaaaa aaaaa SEQ ID NO 5: NDP gene (Mus musculus)
    1 gatgctccat ggaaaagatc cgagcagtgg gcagaggctg
      tgagtccccg ataacgagag 61 cgcctaacat ttccgtggta ttcccatttg ctagagcgct
      gctgcggcca cacgcctgat
```

```
121 tgatatatgc ctgcaatggc actttccat ttgacactct
    ccctctctct ctccctctct
181 ctccctctct ctctctccct ctctctccct
    gggtcgctta aacaacagtc
241 ctaacttttg tgtgttgcaa atataaaagg caagccatgt
    gacagaggga cagaagaaca
301 aaagcatttg gaagtaacag gacctct tc tagctctcag
    aaaagtctga aagaaagga
361 gccctgcgtt tccccaagc tgtgcagcac atactgctgt
    gatcggttgc aagtgaaaga
421 agcaagagaa attcctgcat acaaaggaca atgacaacca
    gaaagcggca gccctatcct
481 gctctggcct tgaaagggac tggatcctag gaggtggcag
    catttccaat ctattgtcct
541 ctgtctccct ctgctgtttt tctggaggag tttccctta
    caacaatgag aaatcatgta
601 ctagctgcat ccatttctat gctctccctg ctggccataa
    tgggagatac agacagcaaa
661 acagacagtt catttctgat ggactctcaa cgctgcatga
    gacaccatta tgtcgattct
721 atcagtcacc cactgtacaa atgtagctca aagatggtgc
    tcctggccag atgtgagggg
781 cactgcagcc aggcatcacg ctctgagccc ttggtgtcct
    tcagcactgt cctcaagcaa
841 cctttccgtt cctcctgtca ctgctgccga ccccagactt
    ccaagctgaa ggctctgcgt
901 ctgcgctgct caggggggcat gcgacttact gccacttacc
    ggtacatcct ctcctgtcac
961 tgtgaggaat gcagctcctg agacttgctg atgattggct
    ttctgactgg cacaaccaca
1021 ggagcagttc aacctgccag agacggactg gcaagaaaag
    agttaaggca gataaagatg
1081 gagcaagtcc cataggattt tgcatattct tgtcctaaag
    actcaatgtg cttttgacag
1141 aaagtgactc tgggaacttg cttttcattc ccatctcctt
    tccctggaag aatttctttt
1201 ggttacttta cagattcagg catttcccct gttggctcta
    attgtggttt gggtgcctga
1261 cagctctgca ttagtgggaa aatgtggggc cctgtgcaat
    agcatgtcag gctgttccta
1321 tttggtgcat attagggaaa attttaccta actctcctta
    ggagatcttt gcttgttgtt
1381 tcccctggtc attttggtct aagatttgcc tctaaagttt
    cctggtttca agatctggac
1441 acccagtcca tggatgttta gtgaggctta ctcacagcca
    gctaactgct actaaaataa
1501 ctaacacatg ggttctttta tgtgacagcg ggactcctga
    ccactatagt aattattcag
1561 aagtgactga ggggatataa atgtggcaga ggaatttata
    atctgaagcc ttttgtgagg
1621 aagcaggctt tcacacatac acactcaggt ggatcctgca
    ctgactctgg agaaggcata
1681 cattatactt ggtgtggaga acacaccata tcataattg
    agcattagtc aagcatgtag
```

```
1741 gaatctactt gtgggtgtgc aatagcttca gccatatctt
    agctatatcc acctgtctat
1801 gtgaagcttg ttgccgtagt ggtggcccga cttattgtct
    gaaattttg tttcaatata
1861 tttttggtcc tcgaagctca aattttgaag tctccccatg
    ttttcaaata aaaatagagt
1921 accttcaaaa aaaaaaaaaa aaaaaaaaaa aa
```

SEQ ID NO 6: NDP gene (*Rattus norvegicus*)
```
   1 cagtgggcag aggctgtgag tcccgataa agagagcgcc
     taacatttcc gtggtattcc
  61 catttgctag tgcgctgctg cggccacacg cctgattgat
     atatgcctgc aatggcactt
 121 ttccatttga cactctccct ctctctcccct ctccctctct
     ctccctctct ctctctccct
 181 ctctctccct gggtcgctta aacaacagtc ctaacttttg
     tgtgttgcaa atataaaagg
 241 caagccatgt gacagaggga cagaagaaca aaagcatttg
     gaagtaacag gacctattc
 301 tagctctcag aaaagtctga aagaaagga gccctgcgtt
     tccccaagc tgtgtagcag
 361 gcactgcggt gatggtgatc ggttgcaagt gaaagaagca
     agacaaactc ctgcatacaa
 421 aggacaatga caaccagaaa acggcagccc catcctgccc
     tggccttgaa agggattgga
 481 tcctaggagg tggcagcatt tcagatctat tgtcctctgt
     cgccctctgc tgttcttctg
 541 gagaagtttc cccttacaac aatgagaaat catgtactag
     ctgcatccat ttctatgctc
 601 tccctgctgg ccataatggg agatacagac agcaaaacag
     acagctcgtt cctgatggac
 661 tctcaacgct gcatgaggca ccattatgtc gattctatca
     gtcacccatt gtacaaatgt
 721 agctcaaaga tggtgctcct ggccagatgt gagggggcact
     gcagccaggc atcacgctct
 781 gaacccttgg tgtccttcag cactgtcctc aagcaaccttt
     tccgttcctc ctgtcactgc
 841 tgccgacccc agacttccaa gctgaaggct ctgcgtctgc
     gttgctcagg gggcatgcga
 901 cttactgcca cttaccggta catcctctcc tgtcactgtg
     aggaatgcag ctcctgaggc
 961 ttgctgatga ttggctttct ggctggcaca accacaggag
     caattcaacc tgctagaaa
1021 ggactggcaa gaaaagagtt aaggcagata aagatggagc
     aagtaccaca ggattgtgca
1081 tactctagtc ctaaagactc gatgtgctt caacagaaag
     tgactctggg agcttgctct
1141 tcattccctt ctcctttctg tggaagaatt tcttttggtt
     acttttcaga ttcaggcatt
1201 tccccttttg gctctgattg tggtttgggt tcctgacagc
     tctgtattag tgggaaaatg
1261 tggggccctg tgcaagagca cgtcaggtgg tccctatttg
     gtgcatatta gggaagaatt
1321 taccgaagtc tccttcagtt gttgtttccc cttgttgttt
     tggtctaaga tttgcacta
```

-continued

```
1381  aaggttccca gtttcaaggt ctggacacca agtccatgga
      tatgtttaga gaggtttact 1441  cacagccagc taactgctac taaataacta acacacgggt
      tatttcatgt gacagcggga 1501  ctcctgacca ctatagttgt tattcagaaa tgacttaggg
      gatataaagg tggcagaagg 1561  aatttataat ctgaagactt ttgcaggtaa atgatggtaa
      acttttgtga ggaagcaggc 1621  tttcacacat atacactcag atggatcctg tcttggctct
      ggagaaggca tacattacat
```

-continued

```
1681  gtggcatgga gaacacatca tactcttgat tgagcattag
      tcaagcatta gtctacttgt 1741  gggtgtgcaa tagcttcagc catatcttga atgtcattcc
      ctaacatcca cctgtctatg 1801  tgaagtttgt tgccataatg gtggcccggc ttatcctctg
      aaaactttgt tttcaatata 1861  cttttagtcc ttgaagctca aattttgaat ctccccatgt
      tttgaaataa aaatagagta 1921  ccttc
```

The invention claimed is:

1. A process of protecting a retina of a subject from neuronal damage comprising:

administering a Norrin protein in a therapeutically effective amount of 1 to 10 nanograms to an eye to said subject, said Norrin protein binds and stimulates signaling via a frizzled-4 cellular receptor and is selected from the group consisting of: one of SEQ ID Nos. 1-3, an N-terminal truncate fragment thereof, and a mutant thereof, said mutant being a SEQ ID. No. 1 mutation of one of: T27A, S28A, S29A; P36A, R37A, R38A; Y120A, R121A, Y122A; H127A, E129A, E130A or combinations thereof;

said administering of said one of SEQ ID Nos. 1-3, said mutant thereof or said combination thereof protecting the retina of the subject from the neuronal damage.

2. The process of claim 1 wherein said administering is by a route selected from the group consisting of: systemic administration, local administration, injection, topical administration, intraocular, and iontophoretic delivery.

3. The process of claim 1 wherein said subject is selected from the group consisting of: cow, horse, sheep, pig, goat, chicken, cat, dog, mouse, guinea pig, hamster, rabbit, and rat.

4. The process of claim 1 wherein said subject is human.

5. The process of claim 1 wherein said Norrin protein is recombinant.

6. The process of claim 1 wherein said Norrin protein further comprises a marker for monitoring function of the said Norrin protein in the subject to whom said Norrin protein has been administered.

7. The process of claim 1 wherein said marker is selected from the group consisting of: green fluorescent protein, luciferase, and β-galactosidase.

8. The process of claim 1 wherein said Norrin protein is packaged into microspheres.

* * * * *